(12) United States Patent
Rumpf et al.

(10) Patent No.: US 8,273,915 B2
(45) Date of Patent: Sep. 25, 2012

(54) PROCESS FOR PREPARING ISOCYANATES

(75) Inventors: Bernd Rumpf, Hockenheim (DE);
Michael Bock, Ruppertsberg (DE);
Martin Fiene, Niederkirchen (DE);
Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 238 days.

(21) Appl. No.: 12/675,095

(22) PCT Filed: Aug. 27, 2008

(86) PCT No.: PCT/EP2008/061188
§ 371 (c)(1),
(2), (4) Date: Feb. 24, 2010

(87) PCT Pub. No.: WO2009/027418
PCT Pub. Date: Mar. 5, 2009

(65) Prior Publication Data
US 2011/0124908 A1    May 26, 2011

(30) Foreign Application Priority Data
Aug. 31, 2007    (EP) .................................... 07115380

(51) Int. Cl.
*C07C 263/00*    (2006.01)
(52) U.S. Cl. ........................................ 560/352; 560/347
(58) Field of Classification Search .................. None
See application file for complete search history.

(56) References Cited

U.S. PATENT DOCUMENTS

| | | | |
|---|---|---|---|
| 3,140,305 A | 7/1964 | Lowenstein | |
| 4,076,577 A * | 2/1978 | Hetzel et al. | 159/47.1 |
| 5,962,728 A * | 10/1999 | Mason et al. | 560/352 |
| 6,506,281 B1 | 1/2003 | Casper et al. | |
| 2006/0089507 A1 | 4/2006 | Sohn et al. | |

FOREIGN PATENT DOCUMENTS

| | | |
|---|---|---|
| DE | 41 27 514 | 2/1993 |
| DE | 41 42 769 | 6/1993 |
| DE | 198 27 852 | 12/1999 |
| DE | 102 60 093 | 7/2004 |
| EP | 1 717 223 | 11/2006 |
| WO | 2004 056757 | 7/2004 |

OTHER PUBLICATIONS

U.S. Appl. No. 13/266,049, filed Oct. 24, 2011, Stroefer, et al.
International Search Report issued Dec. 23, 2008 in PCT/EP08/61188 filed Aug. 27, 2008.
U.S. Appl. No. 12/678,771, filed Mar. 18, 2010, Knoesche, et al.
U.S. Appl. No. 13/380,357, filed Dec. 22, 2011, Schelling, et al.
U.S. Appl. No. 13/380,680, filed Dec. 23, 2011, Schelling, et al.
U.S. Appl. No. 13/383,549, filed Jan. 11, 2012, Schelling, et al.
U.S. Appl. No. 13/383,433, filed Jan. 11, 2012, Schelling, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention provides a process for preparing polyisocyanates, comprising the steps of
a) reacting amines with phosgene,
b) removing hydrogen chloride, excess phosgene and, if appropriate, the solvent from the reaction mixture,
c) separating the liquid mixture from step b) into a liquid phase and a gaseous phase,
d) working up the gaseous phase from step c) to give the polyisocyanate.

20 Claims, 1 Drawing Sheet

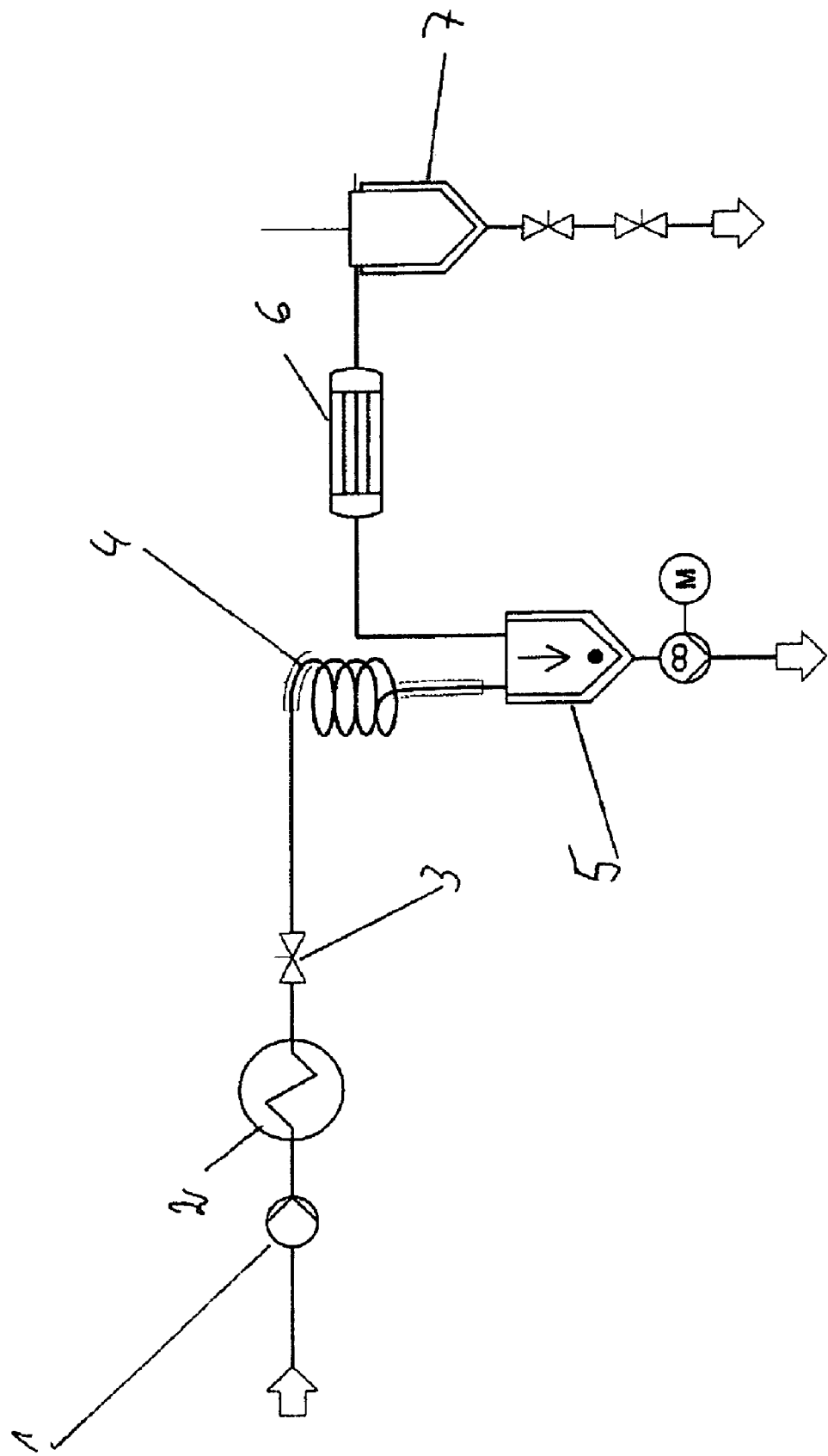

PROCESS FOR PREPARING ISOCYANATES

CROSS REFERENCE TO RELATED APPLICATION

This application is a 371 of PCT/EP08/061188, filed on Aug. 27, 2008, and claims priority to European Patent Application No. 07115380.3, filed on Aug. 31, 2007.

Di- and polyfunctional isocyanates, also referred to hereinafter as polyisocyanates, such as tolylene diisocyanate (TDI), diphenylmethane diisocyanate (MDI), isophorone diisocyanate (IPDI) or hexamethylene diisocyanate (HDI) are valuable starting compounds for the preparation of polyurethanes.

Di- and polyisocyanates and their preparation have been known for some time and described many times. Known processes for preparing isocyanates such as TDI, MDI, IPDI or HDI are usually based on a phosgenation of the corresponding amine with a subsequent removal of the hydrogen chloride and of the excess phosgene. The crude isocyanate/solvent mixture is then subjected to a multistage workup in order to remove the solvent and troublesome low and high boilers. The solvents used for the preparation of the isocyanates are preferably chlorinated aromatic hydrocarbons such as chlorobenzene, dichlorobenzene, trichlorobenzene or aromatic hydrocarbons such as toluene, xylene or benzene. Various processes practiced on the industrial scale for preparing isocyanates are described, for example, in Ullmann's Encyclopedia of Industrial Chemistry.

A disadvantage of the procedure described above is, though, that comparatively large residence times are present in the course of distillation of the pure product, which promotes high boiler formation from the product of value. Moreover, in the course of the procedure described above, high-boiling by-products formed in the reaction get into the workup, which promotes further high boiler formation from the isocyanate product of value.

Accordingly, the yield is, for example, in the process for preparing TDI from tolylenediamine (TDA) usually only about 95%.

These secondary components have the property of reacting with the isocyanates and thus of reducing the proportion of isocyanates in an isocyanate/by-product mixture. The difficult handling and the typical composition of such a residue is stated, for example, in DE 102 60 093 A1.

WO 2004/0456759 A1 describes, for example, the two-stage removal of isocyanates from an isocyanate/high boiler mixture (stream 1). Streams 2 (bottoms) and 3 (distillate) are divided in a weight ratio of from 20:1 to 1:1. In other words, no more than 50% of stream 1 is drawn off via the bottom. The solution is concentrated, pumped into a kneader and concentrated further there.

It was an object of the present invention to develop a process for preparing polyisocyanates which can be operated with a high yield and which, in particular, avoids the yield losses which result in the workup of the crude isocyanate mixture.

It has now been found that, astonishingly, the yield losses mentioned can be reduced effectively when the high-boiling compounds already present in the crude isocyanate mixture, for example ureas and their conversion products formed by phosgenation, i.e. carbodiimides, isocyanurates, uretdiones, are removed with a suitable apparatus design before or during the actual distillation sequence to remove the solvent and the low boilers. In addition, it has been found that a suitable preconcentration can dissociate some of the high-boiling components comprising the isocyanate back to the isocyanate, as a result of which yield losses via the bottom can firstly be reduced effectively, but secondly, contrary to the teaching to date, the bottom product remains free-flowing and hence readily conveyable even at high evaporation rates. Moreover, this prevents monomeric isocyanate from adding onto the high-boiling compounds in the course of workup and hence reducing the yield.

The invention accordingly provides a process for preparing polyisocyanates, comprising the steps of
a) reacting amines with phosgene,
b) removing hydrogen chloride, excess phosgene and, if appropriate, the solvent from the reaction mixture,
c) separating the liquid mixture from step b) into a liquid phase and a gaseous phase,
d) working up the gaseous phase from step c) to give the polyisocyanate.

Step c) can be performed in all apparatus known for this purpose.

For instance, for the low boiler removal from products of value as performed in step c), one or more evaporation steps are suitable. U.S. Pat. No. 3,140,305 describes, for example, the use of a thin-film evaporator to remove the high boilers formed in the reaction. A disadvantage of the process described is, however, the comparatively complicated apparatus design which is costly in its commissioning and in operation, for example owing to an increased maintenance requirement. Also conceivable is, for example, the use of falling-film evaporators. However, when a falling-film evaporator is used, it is expected that the proportion of by-products, owing to the requirement for operation of the apparatus with a pumped circulation system and the resulting residence times, is significantly greater than in a thin-film evaporator. Moreover, falling-film evaporators can be operated only up to certain limiting viscosities, such that the amount of bottom product and hence the loss of isocyanates will be significantly greater.

The advantages mentioned can be avoided by the use of a helical tube evaporator.

Preference is therefore given to performing step c) in a helical tube evaporator. The helical tube evaporator is described, for example, in DE 198 27 852 A1, and in Chem. Ing. Tech (68), 1996, p. 706-710. The helical tube evaporator is a coiled tube with several turns, in which the concentration of a solution is carried out by heating the tube from the outside. At the entrance, by means of superheating of the feed and decompression, a biphasic mixture is introduced into the helical tube evaporator. As a result of the evaporation in the coiled tube, a biphasic flow of high flow rate is generated rapidly, which allows very high heat transfer coefficients to be achieved. Moreover, caused by the high shear forces at the wall, substantial self-cleaning of the tube is achieved. The residence time in the apparatus is very low. At the exit, the biphasic flow is separated in a separator, for example gravitational separator or centrifugal separator.

The pressure downstream of the apparatus for step c), i.e. in the separator, is preferably from 5 to 200 mbar, especially from 5 to 30 mbar.

The temperature at the exit of the apparatus for step c), i.e. in the separator, is preferably from 100 to 300° C., especially from 130 to 250° C.

In an advantageous embodiment of the process according to the invention, the mixture from step b), before step c), is preheated under pressure and decompressed on entry into the apparatus for step c). This is done in an apparatus which is referred to hereinafter as a preheater. The preheater is preferably a heat exchanger. Suitable preheaters are, for example, tube bundle apparatus, plate apparatus, spiral heat transferors or double tube apparatus. The selection, configuration and the design of such apparatus is known to those skilled in the art.

The preheater and the helical tube evaporator can be heated with steam; heating with heat carriers, for example thermal oils, is equally conceivable. In addition, a method thermally integrated in the overall process is also conceivable.

The conditions in the preheater should be selected such that evaporation does not occur at any point in the preheater. On entry of the superheated mixture from the preheater into the apparatus of step c), it is decompressed, which forms a biphasic mixture. This is fed to the apparatus from step c) and concentrated there by supplying further heat. Especially in the case of use of a helical tube evaporator, selection of the geometry, of the total flow rate and of the proportion of gas after the decompression in the tube allow a wavy film flow to be established. As a result, there is intensive mixing of the liquid film, such that temperature and concentration gradients in the film are effectively degraded. Moreover, high shear stresses are present in the region of the wall, such that the buildup of deposits on the heated walls is effectively prevented.

The evaporation rate to be achieved and hence the concentration of the product of value in the bottom product is typically fixed by the selection of the heating temperature and of the pressure at the exit of step c), preferably in the separator, and can be determined, for example, by experiments.

After step c), vapor and liquid are separated from one another. This can be done, for example, in a downstream separator. The vapors can, for example, be condensed in a condenser connected downstream of the separator and be passed to step d), especially the purifying distillation. The mixture is worked up there to give the pure isocyanate.

It is equally possible in principle to transfer the vapors without a further condensation step directly into the purifying distillation of step d).

The bottom product, whose viscosity depends on the evaporation rate, can be discharged from process step c), for example, with the aid of large-mouth gear pumps.

Usually, according to the evaporation rate achieved, the bottom product, i.e. the liquid phase, may still comprise isocyanate and dissociatable fractions of the isocyanate, i.e., in particular, uretdiones and uretonimines bonded covalently to the high molecular weight residue. The resulting yield losses can be reduced by treating the bottom product thermally, especially in a further evaporative concentration step. This can, for example, be done by another evaporative concentration in a helical tube evaporator. The use of mechanically wiped apparatus is also conceivable, such as thin-film evaporators or short-path evaporators. In this case, it may be necessary to add flow aids to the residue obtained or to the bottom product from the first concentration stage. For instance, DE 41 42 769 A1 describes the use of bitumen and DE 41 27 514 A1 the use of MDI or PMDI as flow aids. Equally, the so-called List kneaders or List degassers are conceivable in principle here. If appropriate, it is possible between or after one or both evaporation steps to provide a delay zone, for example a vessel, paddle drier, stirred tank, tubular reactor, helical tube evaporator, heat exchanger, column bottom, extruder or kneader, especially a helical tube evaporator, to promote the dissociation. The residence time in the above examples is preferably 0.5-5 h at temperatures of 120-250° C., especially 159-240° C., and pressures according to the flow aid of 1 mbar-10 bar.

The bottom product can be discharged from the process and sent to a utilization. However, this is less preferred since pure isocyanate and/or isocyanate readily recoverable from the bottom product which are present therein are also discharged in this embodiment.

The remaining bottom products, usually carbodiimides present in polymeric form and polycyclic chlorinated by-products, can, for example, be disposed of by landfill or incinerated. Preferably, it is possible to hydrolyze them to the corresponding amine in a next step. The recovered amine can preferably be recycled into the phosgenation or be reacted with alkylene oxides to give polyether alcohols.

As described, the process according to the invention can be employed in the case of all isocyanates prepared by phosgenation. It is preferably used in the preparation of tolylene diisocyanate (TDI), diphenylmethane diisocyanate (MDI), isophorone diisocyanate (IPDI) or hexamethylene diisocyanate (HDI), especially in the preparation of TDI.

The basic principle of the process according to the invention using a helical tube evaporator is shown in general form in FIG. 1. The crude isocyanate solution is conveyed by means of a pump (1) into a preheater (2) and preheated there under pressure. To this end, the pressure at the pressure-retaining valve (3) is adjusted such that evaporation does not occur at any point in the preheater. The mixture superheated to the pressure upstream of the helical tube evaporator (4) is decompressed at the pressure-retaining valve (3), which forms a biphasic mixture. The mixture is passed to the helical tube evaporator (4) and concentrated there by supplying further heat. As a result, there is intensive mixing of the liquid film, such that temperature and concentration gradients in the film are effectively degraded. Moreover, high shear stresses are present in the region of the wall, such that the buildup of deposits on the heated walls is effectively prevented. The evaporation rate to be achieved and hence the concentration of the product of value in the bottom product is fixed by the selection of the heating temperature and can be determined, for example, by experiments. In the downstream separator (5), vapor and liquid are separated from one another, and the vapors are condensed in the condenser (6) and sent to the purifying distillation downstream of the collector (7).

The concentration is effected at pressures in the separator of from 2 to 100 mbar, preferably at pressures of from 5 to 30 mbar. The exit temperatures from the preheater and the helical tube evaporator are from 100 to 300 degrees, preferably from 130 to 250 degrees.

The evaporation rate (=flow rate of the vapors based on the flow rate of the stream flowing in) is preferably from 85 to 99% by weight, more preferably from 90 to 98% by weight.

The invention will be illustrated in detail by the examples which follow.

EXAMPLE 1

Not Inventive

TDI was synthesized from TDA and phosgene. The reaction effluent comprised 77% TDI, 20% chlorobenzene and 3% unevaporable residue. The toluene solvent was drawn off via the top and TDI in each case via the bottom in two steps in columns K1 (bottom temperature 160° C.) and K2 (bottom temperature 170° C.). In column K3 (bottom temperature 150° C.), TDI was drawn via the top, and the heavy products were drawn off via the bottom in concentrated form and concentrated in a paddle drier (List reactor). The yield of the process was 95 w/w % TDI. The mean thermal stress in three column bottoms K1, K2 and K3 was 160° C. at a cumulative residence time of 4 hours. In the column bottoms, 3.5 w/w % yield was lost through the thermal stress and the associated yield losses as a result of isocyanurate formation.

The viscosity of the bottoms of K3 at 130° C. was approx. 800 mPas (25 w % TDI)

EXAMPLE 2

Inventive

TDI was synthesized from TDA and phosgene as in example 1. The reaction effluent comprised 77% TDI, 20% chlorobenzene and 3% unevaporable residue. In a helical tube evaporator W1, TDI and solvent were drawn via the top upstream of K1. The concentration rate was 96.5%. The pressure in the separator was 5 mbar. The yield of the process was now 96.2%. The viscosity of the bottom product cooled to 80° C. was only 400 mPas (20 w % TDI) and was thus easier to handle.

The solvent was drawn off via the top and TDI via the bottom, again in two steps, in columns K1 and K2 which worked under the conditions as described in example 1. In column K3, which likewise worked under the conditions as in example 1, TDI was drawn via the top, and a now very small amount of TDI and heavy product was drawn off via the bottom of K3 in concentrated form and concentrated in a paddle drier (List reactor) together with the residue of the helical tube evaporator. In the column bottoms of K1, K2 and K3, the concentration of secondary components was so low that no further significant yield-reducing heavy product formation occurred.

The bottoms of the helical tube evaporator were sent to a kneading reactor (List reactor) at 40 mbar and 240° C. The residence time was approx. 2-3 hours. In the feed, 20% TDI and 80% distillation residue were present. At the solids exit of the kneading reactor, only a residue which comprised 40% of the amount used was obtained. The vapors comprised more than 99 w/w % TDI.

EXAMPLE 3

Inventive

TDI was synthesized from TDA and phosgene as in example 1. The reaction effluent comprised 77% TDI, 20% chlorobenzene and 3% unevaporable residue. In the helical tube evaporator W1, TDI and solvent were drawn via the top. The concentration rate was 96.5%. The pressure in the separator was 5 mbar. The yield of the process was now 96.2%. The viscosity of the bottom product cooled to 80° C. was only 400 mPas (20 w % TDI) and was thus easier to handle.

The solvent was drawn off via the top and TDI via the bottom, again in two steps, in columns K1 and K2 which worked under the conditions as described in example 1. In column K3, which worked under the conditions as in example 1, TDI was drawn via the top, and a now very small amount of TDI and heavy product was drawn off via the bottom of K3 in concentrated form and concentrated in a circulation evaporator with a vapor separator together with the residue of the helical tube evaporator. In the column bottoms of K1, K2 and K3, the concentration of secondary components was now so low that no further significant heavy product formation occurred.

The residence time in the circulation evaporator was approx. 1.5 hours. The bottom temperature was 150° C. In the feed, 20% TDI and 80% distillation residue were present. At the entrance of the evaporator, the residue was diluted 1:1 w/w with dichlorobenzene.

At the top of the circulation evaporator, a mixture of dichlorobenzene and TDI was drawn off. At the bottom of the circulation evaporator, a mixture of TDI and residue was drawn off.

As a result of the thermal treatment, 20-25 w/w % of the residue was converted to TDI.

EXAMPLE 4

Inventive

TDI was synthesized from TDA and phosgene as in example 1. The reaction effluent comprised 77% TDI, 20% chlorobenzene and 3% unevaporable residue.

In the helical tube evaporator W1, TDI and solvent were drawn via the top. The concentration rate was 96.5%. The pressure in the separator was 5 mbar. The yield of the process was now 96.2%. The viscosity of the bottom product cooled to 80° C. was only 400 mPas (20 w % TDI) and was thus easier to handle.

The solvent was drawn off via the top and TDI via the bottom, again in two steps, in columns K1 and K2 which worked under the conditions as described in example 1. In column K3, which worked under the conditions as described in example 1, TDI was drawn via the top and a now very small amount of TDI and heavy products was drawn off via the bottom in concentrated form and concentrated in a circulation evaporator with a vapor separator together with the residue of the helical tube evaporator. In the column bottoms of K1, K2 and K3, the concentration of secondary components was so low that no further significant heavy product formation occurred.

The residence time in the circulation evaporator was approx. 1.5 hours. The bottom temperature was 150° C. In the feed, 20% TDI and 80% distillation residue were present. At the entrance of the evaporator, the residue was diluted 1:1 w/w with dibutyl phthalate.

At the top of the circulation evaporator, TDI is drawn off. At the bottom of the circulation evaporator, a mixture of TDI and dibutyl phthalate was drawn off.

As a result of the thermal treatment, 20-25 w/w % of the residue was converted to TDI.

The invention claimed is:

1. A process, comprising
reacting an amine with phosgene to obtain a crude isocyanate mixture comprising an isocyanate, a high-boiling component, hydrogen chloride, unreacted phosgene, and, optionally, solvent,
removing the hydrogen chloride, unreacted phosgene and, optionally, the solvent from the crude isocyanate mixture to obtain a second mixture comprising an isocyanate and a high-boiling component,
preheating the second mixture,
after said preheating, separating, in a helical tube evaporator, the second mixture into a liquid phase comprising the high-boiling component and a gaseous phase comprising the isocyanate, and
isolating the isocyanate from the gaseous phase after said separating.

2. The process according to claim 1, wherein said preheating comprises decompressing the second mixture prior to said separating, thereby forming a biphasic mixture prior to said separating.

3. The process according to claim 1, wherein the pressure downstream of the helical tube evaporating of said separating is from 5 to 200 mbar.

4. The process according to claim 1, wherein the pressure downstream of the helical tube evaporating of said separating is from 5 to 30 mbar.

5. The process according to claim 1, wherein the temperature at the exit of the helical tube evaporating of said separating is from 100 to 300° C.

6. The process according to claim 1, wherein the temperature at the exit of the helical tube evaporating of said separating is from 130 to 250° C.

7. The process according to claim 1, wherein said isolating comprises condensing the gaseous phase obtained from said separating.

8. The process according to claim 1, further comprising thermally treating the liquid phase obtained from said separating to evaporate and obtain isocyanate present in the liquid phase obtained from said separating.

9. The process according to claim 8, wherein the thermal treatment is performed in an apparatus present as a delay zone.

10. The process according to claim 9, wherein the apparatus is a vessel, paddle drier, stirred tank, tubular reactor, helical tube evaporator, heat exchanger, column bottom, extruder or kneader.

11. The process according to claim 8, wherein said thermal treating is performed in a helical tube evaporator.

12. The process according to claim 8, wherein said thermal treating is performed at a temperature of 120-250° C.

13. The process according to claim 8, wherein said thermal treating is performed at a temperature of 150-240° C.

14. The process according to claim 1, further comprising passing the liquid phase obtained from said separating through a thin-film evaporator or short-path evaporator.

15. The process according to claim 1, further comprising hydrolyzing the high-boiling compound present in the liquid phase obtained from said separating to obtain an amine, and recycling the amine into said reacting.

16. The process according to claim 1, wherein the isocyanate is selected from the group consisting of tolylene diisocyanate, diphenylmethane diisocyanate, isophorone diisocyanate and hexamethylene diisocyanate.

17. The process according to claim 1, wherein the isocyanate is tolylene diisocyanate.

18. The process according to claim 1, further comprising, after said removing and before said separating, forming a biphasic mixture comprising a gaseous phase comprising the isocyanate and a liquid phase comprising the high-boiling compound.

19. The process according to claim 1, wherein said isolating comprises condensing and distilling the gaseous phase comprising the isocyanate.

20. The process according to claim 19, wherein the high-boiling component comprises a urea, a carbodiimide, an isocyanurate, a uretdione, or a combination thereof.

* * * * *